United States Patent [19]

Mangia et al.

[11] Patent Number: 4,902,790

[45] Date of Patent: Feb. 20, 1990

[54] NOVEL PROCESS FOR THE SYNTHESIS OF AMIKACIN

[75] Inventors: Alberto Mangia, Milan; Vicenzo Giobbio, Turin; Giorgio Ornato, Ivrea, all of Italy

[73] Assignee: Pierrel Spa, Naples, Italy

[21] Appl. No.: 914,451

[22] Filed: Oct. 2, 1986

[30] Foreign Application Priority Data

Oct. 10, 1985 [IT] Italy .................................. 22425 A/85

[51] Int. Cl.$^4$ ...................... C07H 15/20; C07H 15/22
[52] U.S. Cl. ................................. 536/13.7; 536/13.8
[58] Field of Search ............................. 536/13.8, 13.7

[56] References Cited

U.S. PATENT DOCUMENTS

| | | | |
|---|---|---|---|
| 4,136,254 | 1/1979 | Nagabhushan | 536/13.8 |
| 4,136,254 | 1/1979 | Nagabhushan et al. | 536/13.8 |
| 4,230,847 | 10/1980 | Nagabhushan et al. | 536/13.6 |
| 4,297,485 | 10/1981 | Umezawa et al. | 536/13.6 |
| 4,424,344 | 1/1984 | Kirst et al. | 536/16.9 |
| 4,468,513 | 8/1984 | Kirst et al. | 536/16.9 |

*Primary Examiner*—Ronald W. Griffin
*Assistant Examiner*—Pamela S. Webber
*Attorney, Agent, or Firm*—Nixon & Vanderhye

[57] ABSTRACT

A novel process for the synthesis of amikacin starting from kanamycin A protected at the positions 3 and 6' is described comprising the reaction of kanamycin A with a salt of a bivalent metal cation selected from zinc, nickel, iron, cobalt, manganese, copper and cadmium in the presence of water as the solvent or co-solvent followed by the in situ reaction of the resulting complex with a reactive derivative of L-amino-2-hydroxybutyric acid, removal of the metal cation of the protecting groups and purification of the thus obtained raw product. The acylation under these conditions is extremely selective.

18 Claims, No Drawings

NOVEL PROCESS FOR THE SYNTHESIS OF AMIKACIN

Amikacin [(O-3-amino-3-]-deoxy-alpha-D-glucopiranosyl-(1→6)-O-[6-amino-6-deoxy-alpha-D-glucopiranosyl-(1→4)]-$N^1$-(4-amino-2-hydroxy-1-oxobutyl)-2-deoxy-D-streptamine) having formula (I)

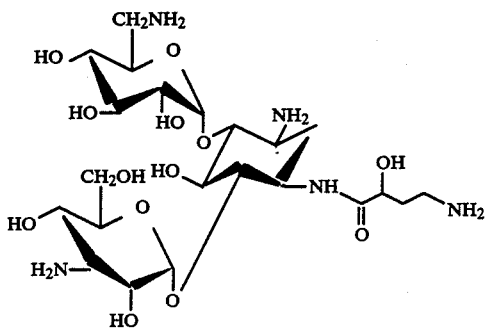

is a semisynthetic antibiotic, widely used in the therapy. Amikacin formally derives from the acylation of kanamycin A (II)

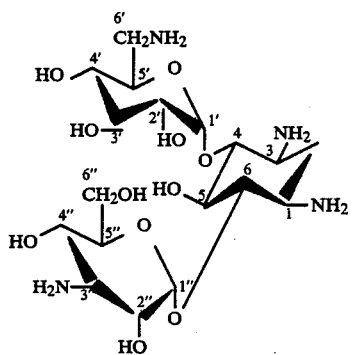

with L-(−)-4-amino-2-hydroxybutyric acid (III) (hereinafter called L-HABA).

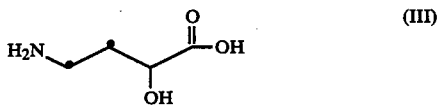

Amikacin was described for the first time in the literature by H. Kawaguchi et al. in Journ. of Antib. XXV, (1972), p. 695 and in the patent literature in the U.S. Pat. No. 3,781,268.

A number of processes however have been described both in patent and in non-patent literature, aiming at the preparation of amikacin with greater and greater yields and purity.

As a matter of fact, as it is noted in the molecule of kanamycin A (II), there are four acylable amino groups, two of them on the central cycle of the 2-deoxystreptamine, respectively called N-1 and N-3, one on the cycle of the 6-amino-6-deoxy-D-glucose, called N-6', and one on the cycle of the 3-amino-3-deoxy-D-glucose called N-3''.

The difficulties in the chemical synthesis of amikacin reside in the regio-selective acylation of the amino group in the position 1; the other three amino groups, if acylated, lead to position isomers with less microbiological activity apart from the consequent reduction of stoichiometrical yield of the main product, namely amikacin.

Moreover the positional isomers present in the synthesis together with amikacin require a fine purification among the several products, which can be obtained only by chromatography on ion exchange resins with a further loss of the yield of the main product.

Besides amikacin, in fact, the following other isomers can be formed, which are acylated with the same group of the L-(−)-4-amino-2-hydroxybutyric acid (T. Naito et al. Journal of Antib. XXVI, 297, (1973):

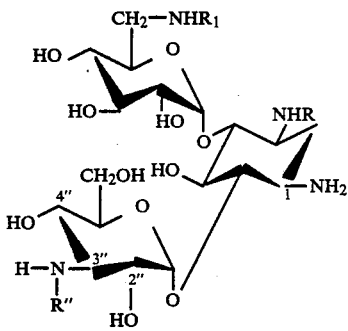

R' = —CO—CH(OH)—CH$_2$CH$_2$NH$_2$
R = R'' = H(indicated as BB-K6)
R'' = —CO—CH(OH)—CH$_2$CH$_2$NH$_2$
R = R' = H(indicated as BB-K11)
R = —CO—CH(OH)—CH$_2$CH$_2$NH$_2$
R' = R'' = H(indicated as BB-K29)

The direct acylation of kanamycin A (for example in T. Naito et al., Journ. of Antib., XXVI, 297 (1973)) leads with high yields mainly to the N-6' acylated derivative, representing the amino group which is more readily reactive; this fact prevents amikacin from being obtained by direct acylation with the L-(−)-4-amino-2-hydroxy-butyric acid.

In practice, when reference is made to the reaction with L-(−)-4-amino-2-hydroxybutyric acid, the reaction is meant with a derivative thereof, wherein the amino group in 4 is protected and the carboxylic group is activated so as to make it readily reactive and with high yield with the amino group of the kanamycin.

More particularly, as protecting groups the usual protecting groups of the amino functions can be selected, which are well known to the skilled in the art such as, for instance, the t-butoxycarbonyl group which can be easily removed at the end of the reaction by treatment with a dilute acid, or the benzyloxycarbonyl group or 4-nitrobenzyloxycarbonyl group which can be removed by catalytic hydrogenolysis on palladium or platinum catalysts, or other like protective groups (see Protective Groups in Organic Synthesis, T. W. Greene; J. Wiley+Sons. Inc., 1981, pages 218–287); however one of the forms in which the carboxylic group is suitably activated is that as active ester with N-hydrophthalimide, N-hydroxy-5-norbornene-2-3-dicarboximide, etc., or as mixed anhydride with pivalic acid, benzoic acid or benzylxcarboxylic acid.

The starting synthesis of amikacin was effected by H. Kawaguchi et al (cited references) by doing away with the serious disadvantage of the greater reactivity of the amino group of the kanamycin in the 6' position by reacting this group with a protective group, such as benzyloxycarbonyl group.

The N-6'benzyloxycarbonylkanamycin (IV) is formed

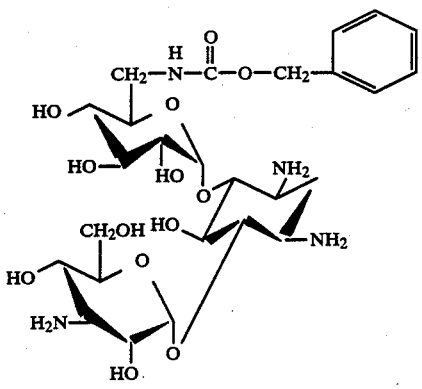

(IV)

which in turn is acylated. This acylation, however, is not regio-selective, whereby, after subsequent hydrogenation to eliminate all the N-benzyloxycarbonylic protecting groups, besides amikacin, also the position isomers BB-K11 and BB-K29 and some polyacylation products are formed. Lacking this selectivity the separation of the thus formed complex mixture is rendered necessary, the separation being carried out on a ion exchange chromatography resin, obtaining raw amikacin with stoichiometrical yields of 22%, which are further reduced by the subsequent purification to obtain pure amikacin. The very low yield of this synthesis caused novel routes to be investigated in order to increase the yield, the costs being consequently reduced, even using a greater number of synthesis steps.

T. Naito, S. Nakagawa and M. Oka in the French published Patent No. 2,272,009 disclosed a further synthesis route by reacting the same 6'N-benzyloxycarbonyl kanamycin A (IV) derivative of the previous synthesis, with some aromatic aldehydes, in a ratio of at least three moles of aldehyde per mole of 6'-N-benzyloxycarbonylkanamycin A, forming the respective Schiff bases between the three free amino groups in the positions 1, 3 and 3" and the and respective aldehydes. The resulting compound (V)

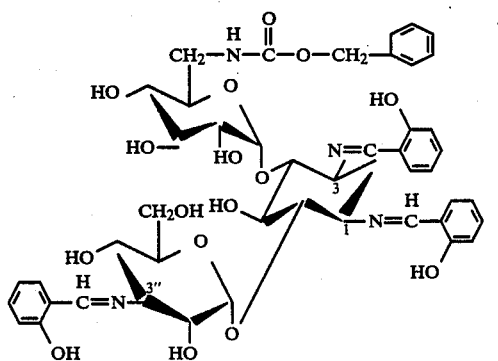

(V)

containing three aldehyde residues per mole of 6'-N-benzyloxycarbonylkanamycin is thereafter acylated with a suitable derivative of L-HABA giving place, after hydrogenolysis of the protective groups, to amikacin.

The acylation of the 3 amino groups (in 1, 3 and 3") however is not selective and it is necessary to make recourse to the chromatography separation on a ion exchange resin to separate amikacin mainly from BB-K29 and BB-K11.

The global stoichiometrical yields of amikacin, moreover, are only of 23%, which are consequently comparable to the yields of previously described method.

Furthermore these yields are calculated on the intermediate (IV), 6'-benzyloxycarbonylkanamycin, which in turn is obtained with stoichiometrical yields of 45–56% from kanamycin A.

Summing up, these two synthesis routes give place to total yields of amikacin starting from kanamycin A, of 10–13%, this value being obviously very low.

A relevant development in the selective acylation of kanamycin A to give amikacin has been achieved with the research of M. J. Cron et al, described in Chem. Comm., 266 (1979), and in the U.S. Pat. Nos. 4,347,354 and 4,424,343.

In these patents the preparation of amikacin is disclosed by acylation of a polysilylated derivative of kanamycin A, which possibly may by provided in 6' or in 6'- and 3- with protective groups different from silyl. More particularly, the preparation of the polysilylated derivative of kanamycin or of protected kanamycin is carried out by reacting the kanamycinic substrate in a suitable organic solvent, among which acetonitrile is preferred, with several silanizing agents, among which hexamethyldisilazane is preferred, to give derivatives wherein all hydroxy groups of the kanamycin or part thereof, are protected with the —Si(CH$_3$)$_3$ group. After the usual hydrogenolysis, in this case only to remove the protecting group of the L-HABA acid, a mixture of positional isomers is still obtained, besides starting kanamycin and polyacylation products, thus rendering still necessary the chromatographic separation of the products. This process, even if causes the yields of amikacin to be remarkably increased, however shows serious drawbacks from the point of view of the environmental safety. More particularly, in fact, acetonitrile, which is the preferred solvent for this reaction, is a highly toxic solvent the use of which at the industrial level is highly unadvisable; moreover, hexamethyldisilazane does form, during the reaction, gaseous ammonia, which must be suitably removed to avoid atmospheric pollution.

A further method for the preparation of amikacin is based on the research work of T. Tsuchiya et, al. Tet. Lett., 4951 (1979) and Belgian Patent No. 879,925 of Zaidan Hojin Biseibutsu Kagaku Kenkyu Kai.

The synthesis route is based on the forming of an intermediate derivative (VI) protected in the positions N-6' and N-3 with the usual N-benzyloxycarbonyl group:

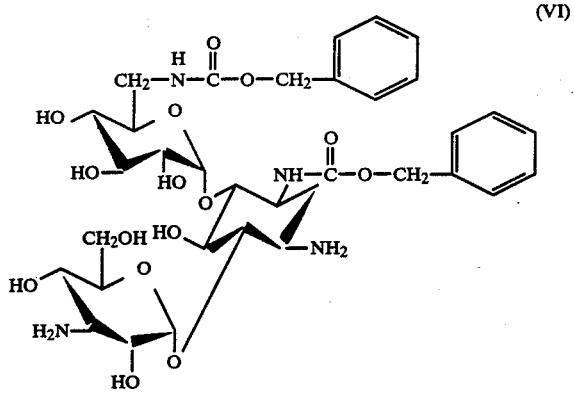 (VI)

This intermediate, obtained by forming complex compounds between amino groups in 3″ and in 1 with zinc acetate and the related hydroxyl groups in vicinal position with respect to the above mentioned amino groups, had already been described in the paper of T. L. Nagabhushan et al. J. Amer. Chem. Soc., 100, 5254 (1978) and in the U.S. Pat. No. 4,136,254 wherein the preparation was reported by means of complexation with several metals.

However, while in the U.S. Pat. No. 4,136,254 this intermediate "di-protected" is converted into the aminoglycosidic antibiotic by direct acylation with an acylating derivative of L-HABA, which however in the case of amikacin gives place to total unsatisfactory yields, in the Belgain Patent No. 879,925 this intermediate is reacted firstly with ethyltrifluoroacetate to protect the amino group in 3″ and then with the derivative of L-HABA which is suitably selected thus giving a selective acylation of the only one free amino group, that in 1. The two different protecting groups, trifluoroacetyl and benzyloxycarbonyl, are then removed with ammonia and hydrogen respectively, thus completing the reaction. In this case too the amikacin yields are increased but, however, the process is not conveniently usable on an industrial scale owing to the use of ethyltrifluoroacetate, which is a highly toxic and extremely expensive reactant.

A novel method for the synthesis of amikacin has now been developed, which is particularly safe from the point of view of the industrial hygienics, since essentially harmless reactants and solvent are used and the intermediates being formed need not be separated. This causes the yield of amikacin to be satisfactorily increased, using at the same time reactants which are much less expensive than those used in the prior art.

More particularly, the process of the present invention, starting from a kanamycin A protected in 6′- and in 3-, comprises reacting it with a salt of a bivalent metal cation selected from zinc, nickel, iron, cobalt, manganese, copper and cadmium or their mixtures, in the presence of water as the solvent or co-solvent of the reaction, followed by the in situ reaction of the resulting complex with the suitably selected reactive derivative of L-HABA. The metal cation is then removed by adding a basic solution until the pH is brought to the value of 9-10. The acylation product is then separated by conventional methods, the groups protecting the amino functions in 6′- and 3- and in the side chain are removed and the raw product thus obtained in purified by chromatography giving place to amikacin with yields close to 50%.

More particularly, as starting product, whatever derivative of kanamycin A, can be used wherein, the amino group in 6′- and in 3- are protected by substitution of a hydrogen atom with an acyl group such as, for example a benzyloxycarbonyl or substituted benzyloxycarbonyl group such as p-nitrobenzyloxycarbonyl or p-methoxybenzyloxycarbonyl, an alkoxy carbonyl group such as t-butoxycarbonyl or t-amyloxycarbonyl, phthaloyl group, and a haloalkylcarbonyl group such as trifluoroacetyl or chloroacetyl, or other suitably protective groups. Preferably, however, the amino groups in 6′ and in 3 shall be protected with benzyloxycarbonyl or substituted benzyloxycarbonyl groups since, as already pointed out, these groups can be readily removed at the end of the reaction by catalytic reduction.

The starting product of this type may be prepared with the method described in Belgian Patent No. 855,704 or by the method described in Canadian Patent No. 1,131,628. More particularly the first step of the process of the present invention is carried out by dissolving starting product, i.e. Kanamycin A protected in both 3 and 6′, and an at least equimolar amount of the selected salt of bivalent metal in water or in a mixture of water with an inert water misicible organic solvent such as for instance dimethylsulfoxide, dimethylformamide, lower aliphatic alcohol, tetrahydrofuran, acetone, acetonitrile etc.

The bivalent metal cation is selected among zinc, nickel, iron, cobalt, manganese, copper and cadmium, wherein the less toxic and more ecomonical cations are obviously preferred, whereas the anion can be whatever organic or inorganic anion, although the anions deriving from weak acids are preferred and particularly the anion deriving from weak organic acids such as acetic acid, propionic acid and benzoic acid, since in general the metal salts of these acids have a greater complexing activity.

The salt is generally used in the ratio in moles with respect to the starting substrate of between 1:1 and 10:1 and preferably between 2:1 and 6:1.

The reaction is suitably carried out at room temperature under stirring. Once the complex is formed, the second step of the process comprises the addition under stirring of a solution or suspension of the predetermined reactive derivative of L-HABA in a polar and aprotic organic solvent. Among the organic solvents which can be suitably used there are included dimethylsulfoxide, acetonitrile, tetrahydrofuran, dimethylformamide, and according to a preferred feature of the invention the halogenated aliphatic hydrocarbons such as methylene chloride, chloroform, 1,2-dichloroethane, etc. Also this second step of the process of the invention is suitably carried out at room temperature.

However in both steps it is possible to moderately heat in order to accelerate the reaction.

After some hours stirring the organic phase possibly present is removed either by distillation if the solvent is low boiling or by mechanical separation and the reaction mixture is added with a basic aqueous solution until the pH is brought to a value of between 9 and 10.

As the basic agent any alkali hydroxide or carbonate can be used or, according to a preferred feature of the invention, $NH_4OH$. The addition of the basic agent causes the complex to be destroyed with the detachment of the metal cation and the precipitation of the 3,6′-diprotected acylation product.

The latter is recovered by filtration and the protective groups in 3 and 6' as well as the protecting group in the side chain are removed according to the conventional methods. For example when, according to a preferred embodiment of the invention, the protective groups are benzyloxy carbonyl groups possibly substituted, they are removed by conventional catalytic hydrogenolysis with a catalyst of platinum, palladium, palladium oxide or platinum oxide or, when these protecting groups are phthaloylic groups, they are simply removed by hydrolysis with hydrazine, or protective t-butoxycarbonyl groups are suitably removed with formic acid, etc.

The thus obtained raw product is then purified by means of chromatographic techniques known in the literature for the purification of amikacin. The acylation carried out according to the process of the present invention on the 3-6'-di-N-protected kanamycin A, after the forming of the complex of the latter with the metal cation, leads to an unexpectedly very high regio-selectivity since amikacin is preferably formed and not BB-K 11 or the product deriving from the double acylation at N-1 and N-3''.

This result is probably obtained owing to a difference of stability of the two complexations sites (N-3''>>N-1) under the foreseen reaction conditions.

This result is presented in the following table wherein the data obtained from the direct acylation of 3-6'-di-N-benzyloxycarbonyl-kanamycin or by complexing the latter with zinc acetate and subsequently acylating with the ester of 4-benzyloxycarbonylamino-2-hydroxybutyric acid with N-hydroxysuccinimide are compared:

| 3,6'-di-N—benzyloxycarbonyl-1-N—[L-(-)-γ-benzyloxycarbonylamino-α-hydroxybutyryl]kanamycin A (% stoich.) | |
|---|---|
| direct acylation | 27 |
| acylation of the complex | 58 |
| unreacted 3,6-di-N—benzyloxy-carbonyl-kanamycin | |
| direct acylation | 25 |
| acylation of the complex | 25 |

It is extremely important to observe the composition of the final reaction mixture after hydrogenolysis of the protecting benzyloxycarbonyl groups, which is practically quantitative under the standard conditions, the latter being shown as an example in the experimental part.

The only pollutant in great amount is kanamycin A which not only does not interfere with the separation of the component in the ion exchange chromatographic column, since it has a residence time in the column lower than that of amikacin, but, after concentration, can be recovered leading to a stoichiometrical yield of amikacin equal to 80% with respect to kanamycin A, which is the most expensive reactant of the synthesis.

The following examples which more detailedly illustrate the process of the present invention, must not be construed as a limitation of the scope thereof.

EXAMPLE 1

5.2 g of 3,6'-di-N-benzyloxycarbonylkanamycin A having a titre of 85% (5.87 mmoles) and 3.9 g of anhydrous zinc acetate (21.3 mmoles) are dissolved in a mixture of dimethyl-sulfoxide (25 ml) and water (70 ml). After two hours stirring at room temperature, the ester of 4-benzyloxycarbonylamino-2-hydroxy-butyric acid with N-hydroxy-succinimide dissolved in methylene chloride (3.28 g in 140 ml) is added.

After 5 hours stirring, the isolation is carried out by distilling the methylene chloride and carrying out percolation under 20° C. of a mixture of water (125 ml) and concentrated ammonia (25 ml). After filtration, washing and drying in oven at 45° C. 6.7 g are obtained of 3,6'-di-N-benzyloxycarbonyl-1-N-[L-(—)-γ benzyloxycarbonylamino-α hydroxybutyril]kanamycin A having a purity of 45% together with 16.8% of the starting 3,6'-di-N-benzyloxycarbonyl kanamycin A. This yield corresponds to 51.4% of the stoichiometrical value.

Part of the thus obtained product is hydrogenated with formic acid and Pd/C giving 164 ml of a water solution containing 6.61 mg/ml of amikacin, 0.4 ml/ml of kanamycin, 0.21 mg/ml of BB-K11 and 1.83 mg/ml of diacylation product with L-HABA in N-1 and N-3''.

The relative purity of amikacin is 73%.

EXAMPLE 2

5.2 g of 3,6'-di-N-benzyloxycarbonylkanamycin A having a title of 85% (5.87 mmoles) are suspended in 20 ml of methanol; zinc acetate (3.9 g as anhydrous product) dissolved in water (80 ml) is quickly added. To the obtained solution after 2 hours stirring at room temperature there are added 3.28 g (9.35 mmoles) of the ester L-(—)-4-carbobenzyloxyamino-2-hydroxybutyric acid with N-hydroxy-succinimide dissolved in 100 ml of methylene chloride in only one time.

After a night at room temperature the mixture is diluted after evaporating the methylene chloride, with water and ammonia (5%, 150 ml).

After filtration of the solid and drying there are obtained 6.5 g of product, with a title of 3,6'-N-benzyloxycarbonyl-1-N-[L-(—)-γ-benzyloxycarbonylamino-α-hydroxybutyril]kanamycin A of 49.8%, corresponding to a stoichiometrical yield of 57%.

The starting product still present corresponds to 17% of the separated product, equal to 25% of the stoichiometrical value.

The obtained product from the acylation is suspended in 100 ml of water 3.5 g of 5% Pd/C are added. 7 ml of formic acid dissolved in 20 ml of water are percolated. After one night stirring, the mixture is filtered and the solid residue is washed with water.

The obtained solution (223 ml) has the following composition:

| | mg/ml | relative % |
|---|---|---|
| Amikacin | 8.2 | 63.3 |
| BB-K29 | 0.3 | 2.3 |
| BB-K11 | 0.3 | 2.3 |
| Diacylated* | 0.69 | 5.3 |
| Kanamycin A | 3.46 | 26.7 |

*Product with the residue of L-HABA in position N-1 and N-3'' with a relative purity of amikacin with respect to its homologues (apart from Kanamycin) higher than 90%.

The solution as such is brought to pH 7 and then percolated through a column filled with weakly acid ion exchange resin in ammonia form. It is eluted with ammonia solution and the fractions containing kanamycin A and amikacin are separated.

From the former combined, evaporated and concentrated, 1.1 g of kanamycin sulphate are obtained after precipitation with methanol from a 20% concentration solution. The fractions containing amikacin are concentrated to 20% and after acidification with 50% sulphuric acid, treatment with carbon and additional of methanol, lead to 2.6 g of amikacin sulphate having a microbiological title of 680 μg/mg.

EXAMPLE 3

This comparison example shows how much the selectivity (and/or stability) of the complexes is basically influenced by the water which, on the contrary to the complexation carried out on kanamycin A (in anhydrous environment), not only is not damaging but on the contrary is necessary to enhance the difference between the two sites of complexation.

As a matter of fact in the absence of water no acylation of the 3,6'-di-N-benzyloxycarbonyl-kanamycin A (VI) takes place in the presence of bivalent cations, probably owing to the forming of a stable complex also at level of N-1 besides that of N-3".

5.2 g of 3,6'-di-N-benzyloxycarbonyl-kanamycin A having a title of 85% (5.87% mmoles) are dissolved in 50 ml of dimethylsulfoxide and the solution is added with 3.9 g (21.9 mmoles) of anhydrous zinc acetate. After two hours of stirring at room temperature the ester of 4-benzyloxycarbonylamino-2-hydroxybutyric acid with N-hydroxysuccinimide dissolved in methylene chloride (3.28 g in 140 ml) is added.

After 5 hours stirring, the isolation is carried out by distilling the methylene chloride and by percolating under 20° C. a mixture of water (125 ml) and concentrated ammonia (25 ml).

The product is filtered, washed and dried in oven at 45° C.

There are obtained 5.7 g of starting product having a title of 80% without trace of acylation in N-1.

Under these conditions the positions N-1 and N-3" are blocked owing the forming of complexes hindering the subsequent acylation.

We claim:

1. A process for the selective synthesis of amikacin from kanamycin A protected in the 3- and 6' positions, said process comprising the steps of:
   reacting kanamycin A protected in the 3- and 6'-positions with a salt of a bivalent metal cation selected from the group consisting of zinc, nickel, iron, cobalt, manganese, copper, cadmium and mixtures thereof in the presence of an effective amount of water as a solvent or co-solvent to form a complex;
   reacting said complex with a derivative of L-(−)-4-amino-2-hydroxybutyric acid wherein the amino group is protected and the carboxyl group is activated; and
   destroying the complex by removing the metal cation and removing the protective groups.

2. A process according to claim 1, wherein said complex is reacted in situ.

3. A process according to claim 1, wherein said complex is formed in water or in a mixture of water and an organic solvent, said solvent being selected from the group consisting of dimethylsulfoxide, dimethylformamide, acetonitrile, acetone, tetrahydrofuran, and lower aliphatic alcohols.

4. A process according to claim 3, wherein said complex is formed in water.

5. A process according to claim 1, wherein said bivalent metal cation is selected from the group consisting of zinc, copper and nickel.

6. A process according to claim 5, wherein said bivalent metal cation is zinc (II).

7. A process according to claim 1, wherein the anion of said salt is an anion derived from a weak organic acid.

8. A process according to claim 7, wherein said anion is selected from the group consisting of acetate, propionate and benzoate.

9. A process according to claim 6, wherein said salt of said bivalent metal is zinc acetate.

10. A process according to claim 1, wherein the protecting groups of the amino functions are unsubstituted or substituted benzyloxycarboxylic groups.

11. A process according to claim 1, wherein the carboxy group of the L-(−)-4-amino-2-hydroxybutyric acid is activated as an active ester with N-hydroxysuccinimide or N-hydroxy-5-norbornene-2,3-dicarboximide, or as a mixed anhydride with phthalic acid, benzoic acid or benzylcarboxylic acid.

12. A process according to claim 11, wherein the carboxyl group is activated as an active ester.

13. A process according to claim 1, wherein said salt of said bivalent metal cation and said starting kanamycin A derivative are used in a molar ratio of between 1:1 and 10:2.

14. A process according to claim 13, wherein said molar ratio between the salt of said bivalent metal cation and the starting kanamycin A derivative is between 2:1 and 6:1.

15. A process according to claim 1, wherein the derivative of L-(−)-4-amino-2-hydroxybutyric acid is used in excess.

16. A process according to claim 15, wherein said excess is between 20% and 60%.

17. A process according to claim 1, wherein said bivalent metal cation is removed from the complex by bringing the pH of the mixture of a value of between 9 and 10.

18. A process according to claim 17, wherein the pH is brought to a value between 9 and 10 by adding a NH₄OH solution.

* * * * *